US008895240B2

(12) United States Patent
Ebersole et al.

(10) Patent No.: US 8,895,240 B2
(45) Date of Patent: *Nov. 25, 2014

(54) METHOD, KIT AND SYSTEM FOR COLLECTING AND PROCESSING SAMPLES FOR DNA AND RNA DETECTION

(75) Inventors: Richard C. Ebersole, Wilmington, DE (US); Jeffrey Allen Rivenbark, Wilmington, DE (US)

(73) Assignee: E I du Pont de Nemours and Company, Wilmington, DE (US)

(*) Notice: Subject to any disclaimer, the term of this patent is extended or adjusted under 35 U.S.C. 154(b) by 439 days.

This patent is subject to a terminal disclaimer.

(21) Appl. No.: 12/467,711

(22) Filed: May 18, 2009

(65) Prior Publication Data
US 2010/0028887 A1 Feb. 4, 2010

Related U.S. Application Data

(60) Provisional application No. 61/128,238, filed on May 19, 2008.

(51) Int. Cl.
| C12Q 1/68 | (2006.01) |
| C12P 19/34 | (2006.01) |
| C07H 21/00 | (2006.01) |
| C07H 21/02 | (2006.01) |
| C07H 21/04 | (2006.01) |
| B01L 3/00 | (2006.01) |

(52) U.S. Cl.
CPC .............. *C12Q 1/6806* (2013.01); *B01L 3/505* (2013.01)
USPC ......... 435/6.1; 536/22.1; 536/23.1; 536/24.3; 536/25.4; 435/91.2

(58) Field of Classification Search
CPC ...... C12Q 1/68; C12Q 1/6806; C12Q 1/6844; C12Q 1/686; C07H 21/00
USPC .......................... 435/6.1; 536/23.1, 24.3, 25.4
See application file for complete search history.

(56) References Cited

U.S. PATENT DOCUMENTS

| 4,683,195 A | | 7/1987 | Mullis et al. | |
| 4,683,202 A | | 7/1987 | Mullis | |
| 4,968,615 A | * | 11/1990 | Koszinowski et al. | 435/91.41 |
| 5,334,499 A | * | 8/1994 | Burdick et al. | 435/6 |
| 5,541,067 A | * | 7/1996 | Perlin | 506/4 |
| 5,589,585 A | * | 12/1996 | Mabilat et al. | 536/24.32 |
| 5,824,535 A | * | 10/1998 | Kou et al. | 435/239 |
| 5,994,056 A | | 11/1999 | Higuchi | |
| 6,037,127 A | | 3/2000 | Ebersole et al. | |
| 6,071,698 A | | 6/2000 | Beck | |
| 6,251,632 B1 | * | 6/2001 | Lillicrap et al. | 435/69.1 |
| 6,793,387 B1 | * | 9/2004 | Neas et al. | 366/160.4 |
| 6,894,156 B2 | | 5/2005 | Ebersole et al. | |
| 7,709,203 B2 | * | 5/2010 | Ebersole et al. | 435/6 |
| 2002/0132769 A1 | * | 9/2002 | Kaleko et al. | 514/12 |
| 2004/0010815 A1 | | 1/2004 | Lange et al. | |
| 2004/0166520 A1 | * | 8/2004 | Connolly | 435/6 |
| 2004/0194156 A1 | * | 9/2004 | Fan | 800/8 |
| 2005/0266468 A1 | | 12/2005 | Bedzyk et al. | |

FOREIGN PATENT DOCUMENTS

| WO | 2008024292 A1 | 2/2008 |
| WO | 2008024293 A1 | 2/2008 |
| WO | 2008024294 A2 | 2/2008 |
| WO | 2008048673 A2 | 4/2008 |

OTHER PUBLICATIONS

Brock, J.A. Special Topics Revciew : Taura syndrome, a disease important to shrimp farms in the Americas. World Journal of Microbiology & Bioitechnology 13 :415-418 (1997).*
Gustafson et al., Detection of *Aeromonas salmonicida* from fish by using polymerase chain reaction amplification of the virulence surface array protein gene. Applied and Environmental Microbiology 58 (12) : 381-38256 (1992).*
Pang et al., Identification of *Vibrio harveyi* using PCR amplification of the toxR gene. Letters in Applied Microbiology 43(3) :249-255(2006).*
Willis et al. Prep-A-Gene : a superior matrix for the purification of DNA and DNA fragments. Biotechniques 9 (1) 92-99 (1990).*
Pioneer Hi-bred International, Inc. Educational Services Program. Module 3 : Strawberry DNA extraction pp. 1-11 (2003)].*
Lo et al.,Detection and tissue tropism of white spot syndrome baculovirus (WSBV) in captured brooders of *Penaeus monodon* with a special emphasis on reproductive organs. Diseases of Aquatic Organisms 30 : 53 (1997).*
Wells et al., Development and application of a polymerase chain reaction assay for the detection and enumeration of bile acid 7a-dehydroxylating bacteria in human feces. Clinica Chimica Acta 331 :127 (2003).*
Brock_Special topic review: Taura syndrome, a disease important to shrimp farms in the Americas World Journal of Microbiology & Biotechnology13_415-418_1997.
Sanger_DNA sequencing with chain-terminating inhibitors ProcNatlAcadScL74_5463-5467_1977.
Goel_Molecular beacon a multitask probe JApplMicrobiol99_435-442_2005.
van Hulten_The White Spot Syndrome Virus DNA Genome Sequence Virology286_7-22_2001.
Yang_Complete Genome Sequence of the Shrimp_JournalofVirology75_11811-11820_2001.
Wongteerasupaya_High variation in repetitive DNA fragment length DisAquatOrg54_253-257_2003.
Gustafson_Detection of *Aeromonas salmonicida* from Fish AppEnvlMicrobiol_58_3816-3825_1992.
Pang_Identification of *Vibrio harveyi* LtrsApplMicrobiol43_249-255_2006.
Mari_Shrimp Taura syndrome virus J. Gen Virol83Pt 4_915-926_ 2002.
Troesch_Mycobacterium Species Identification and Rifampin Resistance JClinMicrobiol37_49-55_1999.

(Continued)

*Primary Examiner* — Ethan C Whisenant

(57) ABSTRACT

This invention relates to a method, kit and system for collecting and processing of samples to release and treat DNA and RNA for gene sequence detection. The method described here in provides for rapid and convenient release, and recovery of DNA and RNA from tissues and cellular materials.

4 Claims, No Drawings

(56) References Cited

OTHER PUBLICATIONS

Anderson, Nadja, What is DNA? DNA extraction from a Kiwifruit. Teacher Guide (Online 2000). Retrieved from the Internet: URL:http://biotech.biology.arizona.edu/labs/DNA_Kiwifruit-teacher.html.

Hameed_A simple PCR procedure to detect white spot AquaticsIntl_p441-450_2005.

International Search Report of corresponding PCT case: European Patent Office in Rijswijk, NL Reuter, Uwe, Authorized Officer Sep. 14, 2009.

Willis_DNA Sequencing Report Prep A Gene BioTechniques9_92-99_1990.

Trobridge_MXmRNAexpressionandRFLPDiseasesofAquaticOrganismsvol. 40_pp1-7_2000.

* cited by examiner

SEQUENCE LISTING

<160> NUMBER OF SEQ ID NOS: 21

<210> SEQ ID NO 1
<211> LENGTH: 24
<212> TYPE: DNA
<213> ORGANISM: Shrimp white spot syndrome virus

<400> SEQUENCE: 1
aagtatttgc cagaagagcc gagg                                          24

<210> SEQ ID NO 2
<211> LENGTH: 24
<212> TYPE: DNA
<213> ORGANISM: Shrimp white spot syndrome virus

<400> SEQUENCE: 2
actggccgaa cacttactat cccg 24

<210> SEQ ID NO 3
<211> LENGTH: 23
<212> TYPE: DNA
<213> ORGANISM: Shrimp white spot syndrome virus

<400> SEQUENCE: 3
ttcatcaggg gcaatacaga cgc 23

<210> SEQ ID NO 4
<211> LENGTH: 24
<212> TYPE: DNA
<213> ORGANISM: Shrimp white spot syndrome virus

<400> SEQUENCE: 4
tagagcagag ggagatttgg gacc 24

<210> SEQ ID NO 5
<211> LENGTH: 24
<212> TYPE: DNA
<213> ORGANISM: Shrimp white spot syndrome virus

<400> SEQUENCE: 5
aggaggagga acaacaacga cacc 24

<210> SEQ ID NO 6
<211> LENGTH: 24
<212> TYPE: DNA
<213> ORGANISM: Shrimp white spot syndrome virus

<400> SEQUENCE: 6
gtgtcaaagg atcaaggagt ggcc 24

<210> SEQ ID NO 7
<211> LENGTH: 23
<212> TYPE: DNA
<213> ORGANISM: Shrimp white spot syndrome virus

<400> SEQUENCE: 7
cactttcctt gtcatcttca tcc 23

<210> SEQ ID NO 8
<211> LENGTH: 23
<212> TYPE: DNA
<213> ORGANISM: Shrimp white spot syndrome virus

<400> SEQUENCE: 8

```
cagatgaaga cgaagaggaa gaa                                              23
```

<210> SEQ ID NO 9
<211> LENGTH: 109
<212> TYPE: DNA
<213> ORGANISM: Shrimp white spot syndrome virus

<400> SEQUENCE: 9

```
aagtatttgc cagaagagcc gaggctgatg aagagttttg cttaacatac ttttcatcga      60
tagttttatt aaataatgta actaaactgg ccgaacactt actatcccg                 109
```

<210> SEQ ID NO 10
<211> LENGTH: 128
<212> TYPE: DNA
<213> ORGANISM: Shrimp white spot syndrome virus

<400> SEQUENCE: 10

```
ttcatcaggg gcaatacaga cgccaaagaa ttggccaaga agaagataca catctggaac      60
gctaatgggt cgcgggaatt tttggacagt agagggttat acgatagagc agagggagat    120
ttgggacc                                                             128
```

<210> SEQ ID NO 11
<211> LENGTH: 148
<212> TYPE: DNA
<213> ORGANISM: Shrimp white spot syndrome virus

<400> SEQUENCE: 11

```
aggaggagga acaacaacga caccaactca accttcacct gacggtggag atggatacgt      60
agatctttct cctcaaaaga aggctgaact aagaactaga gttgcaaacg tcatctttca    120
agaagtgtca aaggatcaag gagtggcc                                       148
```

<210> SEQ ID NO 12
<211> LENGTH: 135
<212> TYPE: DNA
<213> ORGANISM: Shrimp white spot syndrome virus

<400> SEQUENCE: 12

```
ctgctgataa cactttcctt gtcatcttca tcctctacta ctgttgctgt atccttatcc      60
ttatcctcct catcctcttc ctcttcttct tcagcagcag ctacaacagt gacagatgaa    120
gacgaagagg aagaa                                                     135
```

<210> SEQ ID NO 13
<211> LENGTH: 24
<212> TYPE: DNA
<213> ORGANISM: Shrimp white spot syndrome virus

<400> SEQUENCE: 13

```
attttttaaaa aatgtgttta tttt                                           24
```

<210> SEQ ID NO 14
<211> LENGTH: 25
<212> TYPE: DNA
<213> ORGANISM: Shrimp white spot syndrome virus

<400> SEQUENCE: 14

```
tcgatgtctt cgtcaaacgt tgctc                                           25
```

<210> SEQ ID NO 15

```
<211> LENGTH: 24
<212> TYPE: DNA
<213> ORGANISM: Shrimp white spot syndrome virus

<400> SEQUENCE: 15
gaagataccg acatgtattc cgga                                          24

<210> SEQ ID NO 16
<211> LENGTH: 23
<212> TYPE: DNA
<213> ORGANISM: Shrimp white spot syndrome virus

<400> SEQUENCE: 16
ttatccagct ccatgaaaaa aca                                           23

<210> SEQ ID NO 17
<211> LENGTH: 25
<212> TYPE: DNA
<213> ORGANISM: Shrimp white spot syndrome virus

<400> SEQUENCE: 17
ctattgtgca catcaacata tgcca                                         25

<210> SEQ ID NO 18
<211> LENGTH: 25
<212> TYPE: DNA
<213> ORGANISM: Shrimp white spot syndrome virus

<400> SEQUENCE: 18
tgtttggcag taaattgttc attga                                         25

<210> SEQ ID NO 19
<211> LENGTH: 118
<212> TYPE: DNA
<213> ORGANISM: Shrimp white spot syndrome virus

<400> SEQUENCE: 19
atttttaaaa aatgtgttta ttttccccca accttaaaca gatcattgcc aggagaaaat   60
cgcatactta acagataatg cctatttgta tcatcgatgt cttcgtcaaa cgttgctc    118

<210> SEQ ID NO 20
<211> LENGTH: 123
<212> TYPE: DNA
<213> ORGANISM: Shrimp white spot syndrome virus

<400> SEQUENCE: 20
gaagataccg acatgtattc cggagaggat gttgttgtcg tatgggatgg ttgtgatgga   60
ggaaaagtgc taagtgtcac cttcaattgt ggtgataatt ttatccagct ccatgaaaaa  120
aca                                                                123

<210> SEQ ID NO 21
<211> LENGTH: 118
<212> TYPE: DNA
<213> ORGANISM: Shrimp white spot syndrome virus

<400> SEQUENCE: 21
ctattgtgca catcaacata tgccataaaa tcggaatggg tcaagtgcat gtcctttaat   60
ttacccgttt ttgacaagta agtgactggc aactgtttgg cagtaaattg ttcattga   118
```

US 8,895,240 B2

METHOD, KIT AND SYSTEM FOR COLLECTING AND PROCESSING SAMPLES FOR DNA AND RNA DETECTION

CROSS-REFERENCE TO RELATED APPLICATION

This application claims priority under 35 U.S.C. §119 from U.S. Provisional Application Ser. No. 61/128,238, filed May 19, 2008.

FIELD OF THE INVENTION

This invention relates to a method for collecting and processing of biological samples (e.g. plant and animal tissues and the like), for the purpose of analysis or identification (detection) of a particular genomic materials (DNA and RNA); and further relates to a kit and system for performing the method and detection of such materials.

BACKGROUND OF THE INVENTION

Microorganisms from insects, bacterial and viral pathogens are harmful agents which threaten human and animal health and greatly increase the costs and the financial risks of food production. These threats are particularly true in farms and aquaculture and where "livestock" are grown in high intensity production facilities. The detection and identification of these agents by the genomic material via PCR, RT-PCR (wherein PCR means polymerase chain reaction and RT-PCR means reverse transcription PCR) and gene sequencing are now well established and are proving useful in strategies for the detection and control of these agents. However, the application of these methods for direct detection of nucleic acids contained in aquacultural, agricultural, environmental and clinical samples has often proven inefficient and most often not possible.

Many reasons for this detection inefficiency are known. These include the fact that the target nucleic acids are frequently entrapped or compartmentalized inside the microorganism and inside the tissues of the host. This compartmentalization can render the genomic material of the microorganism ("target nucleic acids") unavailable for direct detecting. As consequence, a method to release and solubilize target nucleic acids is needed for detection. In known methods, target nucleic acids are comingled both with inhibitors and with large amounts of host DNA and RNA contained in the cells and tissues, complicating detection of target nucleic acids.

Animal, marine and environmental samples are further complicated by solid sediments, colloids, emulsions, soluble and insoluble salts, biopolymers, biodegraded debris, inert materials and contaminating industrial and natural chemicals in the samples. The heterogeneity and complexity of these samples can inhibit or invalidate direct nucleic acid detection methods. Sample coloration, also can obstruct test results when colors are part of the analysis or detection method.

Direct detection of microorganisms and pathogens is further complicated in many instances, as samples contain only a few copies of the target genomic material. Furthermore, in these samples, the target genomic material is frequently present with large numbers of genomic materials from both the host and non-target organisms present in the samples. Because of the low target copy number and the high concentration of background genomic material and inhibitors, the sensitivity and specificity of direct detection approaches such as PCR, RT-PCR and immunoassays are subject to chemical interferences and inefficiencies in detection.

To circumvent these problems, some form of sample treatment is required to concentrate, purify and free the target genomic material from interfering materials. Many sample preparation approaches have been developed to obviate the inaccuracies and false results due to the loss of sensitivity and compromised specificity resulting from genomic compartmentalization, inhibitors and inefficient genomic detection.

Generally, these treatment processes involve: i) tissue disruption and cell lysis to release the target genomic material, ii) adsorption of the genomic material onto a solid support such as membranes or adsorbent materials, iii) washing the adsorbed genomic material free of contaminants, and iv) releasing the genomic material from the solid support for detection.

Although the methods described above have proven useful for the detection and identification for detection of genomic materials, they still suffer from the need for multistep processes to purify and isolate the genomic material prior to analysis. Such processes not only entail use of supporting equipment and materials, (e.g. centrifugation, membrane filtration and/or chemical precipitation) they may also require toxic chemicals and solvents to stabilize the genomic material and to aid in the release of the genomic material from the solid supports. These methods not only add complexity, cost and time to the analysis but may also need to be practiced in the laboratory using vacuum or electrical equipment.

As a consequence, there is still a need for a method for detection of harmful agents such as microorganisms, including bacterial and viral pathogens, that can be practiced in the field, without need for laboratory vacuum or electricity, is rapid and simple to use, does not require non-toxic chemicals, and is low cost and can be used for the rapid detection and identification of pathogens based on diagnostic gene sequences. By "field" it is meant, for example, a site for growth or production or processing of food products, including but not limited to farms (both aquaculture and agriculture), food processing and packaging sites, and the like.

To monitor and control detrimental microorganism and to control diseases they cause, there is further a need for a simple sample processing technology which can be used in the field to collect, process and recover genomic materials from samples in which microorganisms be found for analysis of a target nucleic acid of the microorganism.

The present invention meets these needs.

SUMMARY OF THE INVENTION

The present invention addresses the problems described above by providing a flexible-walled vessel and method for collecting and processing nucleic acids from a sample and a diagnostic system suitable for use with the method, which comprises a kit, wherein the method can be performed at low cost, is simple to use and can be used in the field. The method comprises collection and processing of genomic materials, which are nucleic acids) from a sample without need for purification of the sample genomic material. The method can be used with a kit to provide low cost, rapid on-site (in the field) detection of bacterial and viral pathogens contained in animal and plant fluids or tissues.

It is an object of the present invention to provide an effective, uncomplicated, rapid and inexpensive vessel and method to collect and recover nucleic acids from samples for analysis of a target nucleic acid, or a particular gene sequence or for identification. The method is capable of use in the field. It is a further object to provide a method to release and solubilize nucleic acids and free them from interfering solutes and inhibitors which inhibit or diminish their detection. It is a still further object to provide an inexpensive kit and diagnostic system to accomplish the foregoing objectives.

The present invention provides a method, kit and system for collection, processing and analysis of a target nucleic acid from a sample. The method comprises (a) providing a sample comprising nucleic acids; (b) transferring the sample to a flexible-walled vessel; (c) adding an extraction fluid to the vessel; (d) processing the sample with the extraction fluid and one or more treatment reagents in the vessel to release nucleic acid from the sample to solubilize the nucleic acid and produce a recovery fluid; and (e) transferring a portion of the recovery fluid or product from step (d) to a suitable detection system for detection of the target nucleic acid.

By "processing" in step (d), it is meant herein to including mixing the sample with the extraction fluid and treatment reagent(s) and optionally, treating the mixture such as, by macerating the sample with the extraction fluid and treatment reagent(s).

Optionally, the one or more treatment reagents may be added to the vessel prior to transferring the sample to the vessel. The one or more treatment reagents may aid in the release and solubilization of the nucleic acids and/or the removal or inactivation of inhibitory substances ("inhibitors") that interfere with the subsequent detection of gene sequences in the target nucleic acid. The flexible-walled vessel may also be heated or cooled to deactivate inhibitors and/or preserve or stabilize the nucleic acids.

Optionally, the flexible-walled vessel may contain filter media to facilitate sample filtration after nucleic acids have been released and solubilized after step (d) and before step (e), to eliminate particulates.

Suitable detection systems use PCR, RT-PCR, isothermal amplification, gene sequencing or probe hybridization technology.

Also provided is a kit which provides materials and a vessel to prepare samples and to detect or identify a diagnostic target DNA or RNA via PCR, RT-PCR, isothermal amplification, gene sequencing or probe hybridization technology. The kit comprises (a) a flexible-walled vessel in which a sample is processed, (b) an extraction fluid, (c) one or more treatment reagents and (d) a pipette to collect and measure a recovery fluid produced by processing the sample with the extraction fluid and treatment reagent(s) in the vessel, and to transfer the recovery fluid to a suitable detection system. The kit may further comprise a crushing device to aid in crushing solid sample, and a filtration device.

The kit may further comprise detection media comprising one or more detection reagents for the detection and identification of the PCR, RT-PCR, isothermal amplification, gene sequencing or probe hybridization products.

The kit typically further comprises instructions that describe method to use the components of the kit for sample preparation and detection of a diagnostic target DNA or RNA nucleic acid.

Also provided is a diagnostic system providing for both sample preparation and detection or identification of a target nucleic acid contained in a sample. The system comprises the kit as described hereinabove, and a detection system. The detection system depends on whether the target nucleic acid is a DNA or RNA, or cDNA product. The detection system or the kit comprises detection media. The detection system comprises a processor for detection of the DNA or RNA, or cDNA product. Detection can be accomplished using PCR, RT-PCR, isothermal amplification, gene sequencing or probe hybridization technology. The processor for accomplishing the detection comprises a thermocycler or an oven heater.

The detection system further comprises a detection method. The detection method can be selected from standard non-denaturing gel electrophoresis (e.g., acrylamide or agarose), denaturing gradient gel electrophoresis, temperature gradient gel electrophoresis, capillary electrophoresis, or fluorescence detection.

Terminology and Abbreviations

The following abbreviations and definitions are to be used for the interpretation of the claims and the specification.
dNTP Nucleotide
DNA Deoxyribonucleic acid
PCR polymerase chain reaction
RNA Ribonucleic acid
DNase Deoxyribonuclease
RNase Ribonuclease
RT Reverse transcription
RT-PCR Reverse transcription polymerase chain reaction

DEFINITIONS

As used herein, the term microorganism means any bacterium, virus, eukaryotic or prokaryotic organism cell having DNA or RNA suitable for analysis or detection. The microorganism may be living, dead, or damaged, that is, having disruptions in the cell wall or cell membrane. In particular, as regards to shrimp aquaculture, particularly notable microorganisms which are pathogens include white spot syndrome virus ("WSSV"); infectious hypodermal and hematopoietic necrosis virus ("IHHNV"); taura syndrome virus ("TSV"); and *Vibrio harveyi* (gram-negative bacterium). Diagnostic target DNA or RNA and/or fragments thereof that are diagnostic of the particular pathogen are know. See for example, WO 2008/024294 (for WSSV); WO 2008/024293 (for IHHNV); WO 2008/024292 (for TSV); and WO 2008/048673 (for *Vibrio harveyi*). Other pathogens for shrimp and other livestock can be similarly detected using the method, kit and diagnostic system disclosed herein, as will be appreciated by one skilled in the art.

As used herein, the term "DNA" refers to a nucleic acid molecule comprising a deoxyribose sugar as opposed to "RNA" which has a ribose sugar. As used herein, "DNA" and "RNA" refer to all species of DNA and RNA, respectively, including messenger RNA (mRNA), ribosomal RNA (rRNA), transfer RNA (tRNA) as well as small RNA species that have regulatory function. "Small RNA species" have a specific meaning and refer to untranslated RNAs with housekeeping or regulatory roles in bacteria. "Small RNA species" are not rRNA or tRNA.

As used herein, the term "inhibitor" refers to a chemical or other agent having the ability to interfere with the action of PCR or RT-PCR As used herein, the term "RNase inhibitor" refers to a chemical or other agent having the ability to interfere with the action of RNase enzymes, such as the endogenous RNases produced by most bacterial cells. For clarification, RNase is a ribonuclease, which is an enzyme that catalyzes the cleavage of nucleotides in RNA.

The term "target nucleic acid" refers to a DNA or RNA nucleic acid or a DNA or RNA fragment for detection using PCR, RT-PCR, isothermal amplification, gene sequencing or probe hybridization technology in the method, the kit and the diagnostic system of this invention. The target nucleic acid can be a gene sequence.

As used herein, the term "diagnostic target DNA or RNA" refers respectively, to a DNA or RNA molecule or fragment that is diagnostic of a particular microorganism, pathogen or disease. In general, the target nucleic acid is a diagnostic target DNA or RNA.

As used herein, the term "diagnostic target DNA product" refers to a DNA molecule or fragment that is transcribed from a diagnostic target RNA or is synthesized using transcribed DNA copies of the diagnostic target RNA as template.

As used herein, the term "reverse transcription followed by polymerase chain reaction", or "RT-PCR", refers to a technique for synthesizing and amplifying a DNA molecule with a sequence that is a copy of an RNA sequence. RT-PCR is useful for detecting RNA species such as in quantitative analysis of gene expression, as well as for producing DNA copies of RNA for use in cloning, cDNA library construction, probe synthesis, and signal amplification in situ hybridizations. The technique consists of two parts: synthesis of cDNA from RNA by reverse transcription (RT), and amplification of a specific cDNA by polymerase chain reaction (PCR). Reverse transcriptase is an RNA-dependent DNA polymerase that catalyses the polymerization of nucleotides using template RNA or the RNA molecule in an RNA:DNA hybrid.

As used herein, the term "primer" refers to an oligonucleotide, synthetic or naturally occurring, which is capable of acting as a point of initiation of nucleic acid synthesis or replication along a template strand when placed under conditions in which the synthesis of a complementary strand is catalyzed by a polymerase. Within the context of reverse transcription, primers are composed of nucleic acids and prime on RNA templates. Within the context of PCR, primers are composed of nucleic acids and prime on DNA templates.

As used herein, the term "amplification product" refers to nucleic acid fragments that are produced during a primer directed amplification reaction. Typical methods of primer-directed amplification include polymerase chain reaction (PCR), RT-PCR, ligase chain reaction (LCR) or strand displacement amplification (SDA).

As used herein, the term "lysis" means perturbation or alteration to a cell wall facilitating access to or release of the cellular RNA or DNA. Neither complete disruption nor breakage of the cell wall is an essential requirement to the concept of lysis.

As used herein, the term "lysing agent" means any agent or condition, or combination of agents or conditions, suitable for the lysing or opening of cell walls. Lysing agents may comprise enzymes (such as lysozyme, or a bacteriophage lytic enzyme) or chemicals (such as chloroform), detergents, lysing buffers, heat or may involve physical shearing means such as the use of sonication, bead mills, French presses and the like. Lysing agents are well known in the art.

As used herein, the term "thermocycling" refers to the entire pattern of changing temperature used during an RT-PCR or PCR assay. This process is common and well known in the art. See, for example, Sambrook, J., Fritsch, E. F. and Maniatis, T., *Molecular Cloning: A Laboratory Manual*, Cold Spring Harbor Laboratory Press, Cold Spring Harbor, N.Y., 1989; and U.S. Pat. No. 4,683,202 to Mullis, et al. and U.S. Pat. No. 4,683,195 to Mullis, et al. In general, PCR thermocycling includes an initial denaturing step at high temperature, followed by a repetitive series of temperature cycles designed to allow template denaturation, primer annealing, and extension of the annealed primers by the polymerase.

As used herein, the term "direct detection" refers to the assay for the detection and/or identification of the presence of a diagnostic target DNA or RNA without isolation or purification of the diagnostic target DNA or RNA.

DETAILED DESCRIPTION OF THE INVENTION

The present invention provides a method for detecting harmful agents, such as microorganisms, including bacterial and viral pathogens, and a kit and a system suitable for use with the method. In particular, the invention may be applied to detection of pathogens that are, or may be, causative agents of disease. The method comprises collection, treatment and detection of a target nucleic acid (DNA or RNA) or in a sample that is representative of the presence of a harmful agent, without need for purification of the sample. The method and kit and system provide low cost, rapid on-site (in the field) detection of viral and bacterial pathogens contained in animal and plant tissues.

The present invention provides a method, kit and system for collection, analysis or identification of a target nucleic acid from a sample. The gene sequence is used to detect and identify harmful agents present in a sample. The method comprises (a) providing a sample comprising nucleic acids; (b) transferring the sample to a flexible-walled vessel; (c) adding an extraction fluid to the vessel; (d) processing the sample with the extraction fluid and one or more treatment reagents in the vessel to release nucleic acid from the sample to solubilize the nucleic acid and produce a recovery fluid; and (e) transferring a portion of the recovery fluid or product from step (d) to a suitable detection system for detection of the target nucleic acid. Thus, the method of this invention provides for direct detection. There is no need for purification of the target nucleic acid.

By "processing" in step (d), it is meant herein to including mixing the sample with the extraction fluid and treatment reagent(s). Recovery of nucleic acids can be aided by shaking the vessel as part of mixing. Processing may comprise additional treatment steps, such as macerating the sample with the extraction fluid and treatment reagent(s). By "macerating" it is meant to crush or break up solids in the sample to aid in release of the nucleic acid from the sample. Macerating may be useful, when the sample is a solid, such as a biological tissue. Macerating may be accomplished, for example, by applying an external force to the walls of the vessel. During macerating, the walls of the vessel may be brought in contact, causing the sample to be crushed or macerated between the walls of the vessel. The tissues and cell membranes can be altered or disrupted so that the target nucleic acids contained therein can be made available to dissolve in the extraction fluid. Thus, this optional step aids in solubilization and recovery of the nucleic acid. If the sample is a homogeneous fluid, such as blood or hemolymph, crushing may not be necessary.

Treatment reagents may include enzymes or other reagents. Treatment reagents may be used to treat or degrade inhibitors. In addition, treatment reagents may be inactivated prior to step (e) so that they do not negatively affect the subsequent detection of the target nucleic acids.

In step (e), a portion of the recovery liquid in step (d) is transferred to a suitable detection system for detection and/or identification of the target nucleic acids. Suitable detection systems are based on PCR, RT-PCR, isothermal amplification, gene sequencing or probe hybridization technology.

Optionally, the recovery of nucleic acids can be enhanced further by incubating and/or heating the sample and extraction fluid in the vessel. The desired duration of incubation and/or heating depends on the characteristics and type of inhibitors contained in the sample. For example, the extent of incubation and/or heating depends on the time and temperature required to inactivate or degrade inhibitors. Heating may also be used to deactivate treatment reagents such as enzymes used to inactivate or degrade the inhibitors.

The preferred detection system for detection of the target nucleic acid uses PCR or RT-PCR for amplification of the target nucleic acid using diagnostic primer sequences for WSSV, IHHNV, TSV and *Vibrio harveyi* are described more fully in WO 2008/024294 (for WSSV); WO 2008/024293 (for IHHNV); WO 2008/024292 (for TSV); and WO 2008/048673 (for *Vibrio harveyi*).

A kit of this invention comprises materials and a vessel to prepare samples and for detection or identification of a diagnostic target DNA or RNA, for example, via PCR, RT-PCR, isothermal amplification, gene sequencing or probe hybridization technology. The kit comprises (a) a flexible-walled vessel into which a sample is added, (b) an extraction fluid, (c) treatment reagents, (d) a pipette to collect and measure a recovery fluid prepared by mixing the sample with the extraction fluid in the vessel and to also transfer the contents of the vessel to a detection system.

The sample, flexible-walled vessel, extraction fluid and detection system are described hereinbelow. The pipette can be any device that is capable of transferring fluid from one vessel to another. An example of a useful pipette is an accurate volume pipette, such as those commercially available from Poly-Pipets, Inc., Englewood Cliffs, N.J.

The kit may further comprise a crushing device to aid in crushing solid sample, a filtration device and/or filtration media and one or more treatment reagents to aid in the release and solubilization of the nucleic acids and the removal or inactivation of inhibitory substances.

The kit typically further comprises instructions that describe method to use the components of the kit for sample preparation.

The kit for the detection of a target nucleic acid may comprise detection media in either dry or liquid form for the hybridization of target and probe nucleic acids, as well as for the removal of undesirable and non-hybridized forms by washing. The kit may comprise a solid support (e.g., dipstick, bead, and the like) upon which is fixed (or to which is conjugated) unlabeled nucleic acid probe(s) that is (are) derived from isolated diagnostic primer sequences. The kit may further comprise a labeled probe that is complementary to a second and different region of the same DNA strand to which the unlabeled nucleic acid probe is hybridized. The labeled probe may also be derived from the isolated diagnostic primer sequences disclosed herein.

The kit may further comprise detection media for use with the detection system. The detection media may comprise enzymes, deoxynucleotide triphosphates, fluorescence agent, at least one pair of internal sample control primers, at least one internal template control and at least one pair of internal template control primers, and a probe comprising a complementary sequence to a portion of at least one region of the target nucleic acid, which is capable of being amplified with the diagnostic primer sequences contained in the kit. The detection media may be in various forms, such as a liquid, dried, or tablet and may be present in any suitable container or multiple containers, such as vials, tubes, and the like.

Also provided is a diagnostic system providing for both sample preparation and detection or identification of a target nucleic acids contained in a sample. The system comprises the kit as described hereinabove, a detection medium comprising one or more detection reagents for detection of a diagnostic target nucleic acid, and a processor for detection of the DNA or RNA, or cDNA product. The processor for accomplishing the detection comprises a thermocycler or an oven heater.

Following amplification, e.g., using PCR or RT-PCR, the amplified nucleotide sequence may be ligated to a suitable vector followed by transformation of a suitable host organism with said vector. One thereby ensures a more readily available supply of the amplified sequence. Alternatively, following amplification, the amplified sequence or a portion thereof may be chemically synthesized for use as a nucleotide probe for use in a hybridization assay, as described below. In either situation the DNA sequence of the variable region may be established using methods such as the dideoxy method (Sanger, F. et al. Proc. Natl. Acad. Sci. 74:5463-5467 (1977)). The sequence obtained is used to guide the choice of the probe for the organism and the most appropriate sequence(s) is/are selected.

Sample

Generally, the sample is provided from food production, that is, a food or liquid in contact with food, aquaculture, agriculture, industrial processes for food production, and from the environment. This list is exemplary not exhaustive. Of particular interest and application are the recovery of target nucleic acid from samples associated with growth of cultivated livestock or aquaculture. These include food and feed production and the processing, handling and preparation of food. Samples of particular concern for the spread of and contamination due to pathogens are associated with marine aquaculture and in the food supply. Generally, the sample contains water, feed, brood stock, animal tissues, body fluid and/or produced food.

A sample may be provided by collecting a tissue or body fluid, extracting a solid or semi-solid sample, by swabbing a surface. Other techniques are known to those skilled in the art. In one preferred embodiment, the sample is a shrimp tissue, more particularly, one or more shrimp pleopods. Shrimp pleopods can be used in this invention to detect common pathogens in shrimp. More particularly, White Spot Syndrome Virus (WSSV) can be detected in shrimp at a shrimp farm or other shrimp facility or location using the method, kit and diagnostic system of this invention.

Flexible-Walled Vessel

A flexible collection vessel is used to collect, process and recover target nucleic acids for their detection or identification. The vessel has walls that are sealed to form a pouch, open at one end—the top—and provides a liquid tight container.

A primary and essential feature of the vessel is that walls are flexible. This flexibility provides for the following functions.

(i) An external force can be applied to the walls of the vessel so that the solid samples (e.g., biological tissue) can be crushed between the walls. Thus, recovery of target nucleic acids is enabled and improved, by reducing particle size of sample materials, macerating tissues structures and disrupting the cell walls of biological sample materials.

(ii) The vessel's flexibility provides for various means of collecting sample. For example, a flexible vessel can be inverted so that the exterior wall becomes the interior wall. Once the walls are inverted, an operator can place a hand inside the inverted vessel, pick up, sample material, then revert the walls of the vessel back to its initial side and thus bring sample into the vessel. Thus, an operator avoids contaminating the sample with his or her hands. This particular technique can be used advantageously in sampling marine and agriculture organisms. For example, shrimp pleopods can be readily removed from the shrimp and placed in the vessel without need to use other collection aids such scalpels or tweezers.

(iii) The flexibility of the vessel also provide a means of agitating and suspending sample materials in the extraction fluid. By simply applying and releasing an external pressure to the walls, the sample materials can be agitated and suspended in the extraction fluid.

To enhance utility in the method and kit and system of this invention, the flexible vessel preferably has a closure attached to the top of the vessel so that the vessel can be reversibly opened and closed during the method. The closure enables both containment and access to the sample and the recovery fluid through the method steps, which may include collecting material, mixing the sample and extraction fluid, and adding treatment reagents to the sample as well as preventing spillage and contamination of the contents of the vessel. Various closure mechanisms can be used. Fine rib and groove profile type and zipper lock bags are preferred.

The walls of the vessel can be prepared using a variety of synthetic polymer and naturally-derived polymers (e.g. cellophane). Generally, polypropylene and polyethylene are preferred. To maintain flexibility and provide for suitable strength, the wall thickness is generally between 1 and 8 mils (0.025 to 0.20 mm) with wall thickness of 2 to 6 mils (0.51 to 0.15 mm) being preferred. While not wanting to be limiting, the size of the vessel is generally sufficiently large to contain between 0.5 to 1,000 mL with 1 to 15 mL volume being preferred.

Extraction Fluid

An extraction fluid is added to both dissolve any treatment reagents present in the vessel or added to the vessel and to solubilize target nucleic acids contained in the sample. The extraction fluid may both solubilize and chemically treat the sample to enhance recovery of nucleic aids. The extraction fluid may comprise one or more treatment reagents to inactivate or degrade components of the sample which inhibit detection of the nucleic acids ("inhibitors").

The extraction fluid is a fluid. The extraction fluid may be water. The extraction fluid may comprise water and one or more treatment reagents. The extraction fluid is added to the flexible vessel to dissolve and to recover, from the sample, a target nucleic acid. Since this fluid may be transferred to the detection medium, its chemical composition must be compatible with and not interfere with the detection system (based on PCR, RT-PCR, isothermal amplification, probe hybridization, or gene sequencing) including reactions in the system. The product of mixing the sample with the extraction fluid is referred to herein as the "recovery fluid". The recovery fluid thus comprises nucleic acids which have been released and solubilized from the sample.

In a preferred embodiment the recovery fluid serves as the sole diluent for a detection medium which comprises one or more detection reagents, such as a dried or lyophilize detection reagent composition. In this way, detection can be achieved simply without subsequent steps by adding a separate detection fluid to dry detection reagents.

It is further required that the volume of the extraction fluid be sufficient to efficiently extract the target nucleic acid from the sample, while at the same time be sufficient to dilute inhibitors in the sample so that inhibitors do not interfere with detection. Generally the volume of the extraction fluid should be in the range of 25 to 500 times the volume of the detection reaction volume. More preferably, the volume of the extraction fluid should be in the range 50 to 200 times the detection reaction volume.

Treatment Reagents

The kit may also comprise one or more treatment reagents to assist with the solubilizing nucleic acids for their detection and identification of by PCR, RT-PCR, isothermal amplification, gene sequencing, or probe hybridization. One or more treatment reagents are added to perform two distinct functions. First, treatment reagent is added to release and solubilize the target nucleic acid from the sample. The second function of a treatment reagent is to support the amplification of the target nucleic acid.

Typically, more than one treatment reagent is added. For example, a first treatment reagent can be a composition comprising a lysing agent, which is useful for breaking open cell walls to access the target nucleic acid. The lysing agent can be or comprise a detergent, an enzyme, or a combination thereof. The detergent can be a surfactant which aids in solubilizing the target nucleic acid. Enzymes may also assist with the extraction fluid by causing proteins to precipitate or otherwise remove or inactivate inhibitors. Various enzymes and other solubilizing reagents may be immobilized on a support, to help filter particulates. Thus, samples can be treated and treatment reagents removed prior to transferring the sample to a detection system. Additional lysing agents are described, for example, in US 2005/0266468 A1, the teachings of which are incorporated herein by reference.

A second treatment reagent can be a composition comprising a buffer having pH in the range of 7 to 7.8, magnesium chloride, and potassium chloride. This compositions aids in the amplification of the target nucleic acid.

The treatment reagent can further comprise stabilizers which inhibit RNases and DNases.

While not intending to be limiting, a useful composition of the recovery fluid is 50 mM Tris-HCl buffer, 3.0 mM $MgCl_2$, 28 mM KCl, 0.1% Triton X-100 surfactant (Triton X-100 is a surfactant available from Dow Chemical Co., Midland Mich.).

One or more of the treatment reagents can be added to the flexible-walled vessel prior to adding the sample and extraction fluid. In addition, or alternatively the treatment reagents can be added to the extraction fluid.

Filtration

Optionally, the method of the invention comprises a step of filtering the recovery fluid to remove unwanted particulates prior to adding this fluid to the detection system. Unwanted particulates in the recovery fluid may include inhibitors and disproportionate amounts of target nucleic acid. Filtration can thus help to remove inhibitor and to improve test reproducibility.

Filtration can be readily achieved by incorporating a filtration medium in the kit, for example, within the flexible vessel. The method may comprise drawing the recovery fluid through a filter in the flexible vessel. Alternately, the kit may comprise a transfer pipette, wherein the transfer pipette has filtration media within the pipette. Filtering occurs by transferring the recovery fluid through filtration media in a transfer pipette and transferring the filtered fluid to a detection system. The filter should be removed prior to dispensing the recovery fluid into the detection system.

The kit may also comprise filtration media and/or particulates which may be sorbents or non-sorbents. Filtration media and particulates can also be added to the vessel or used in the method to remove inhibitors and/or to aid in the filtration process.

Filtration media include fabricated or nonfabricated natural fibers and non-woven synthetic fibers. These materials may be treated or untreated to aid in sample compatibility and wetting. For example, fibers such as cotton and nylon can be used.

Filtration particulates include sorbents and non-sorbent particles, which may be used to adsorb and remove unwanted material from the recovery fluid or be used to aid filtration. Sorbent and non-sorbent particles may be used in combination with filtration media. Sorbents should have a density greater than 1.0 g per cc. Specific sorbents include J. T. Baker diatomaceous earth (cat. #1939-01), CELITE4/4, KENITE4/4 200, CELATOM4/4 FW6, CUNO4/4 M-901, CUNO4/4 m802, PERFLO4/4 200, PERFLO4/4 63, PER- FLO4/4 30, ALITE4/4 150, ALITE4/4 180, or mixtures thereof, J. T. Baker diatomaceous earth (cat. #1939-01), CELITE4/4, KENITE4/4 200, CELATOM4/4 FW6, CUNO4/4 M-901, CUNO4/4 m802, PERFLO4/4 200, PERFLO4/4 63, and PERFLO4/4 30 sorbents.

While the amount of filtration media or particulates to use depends on the size of the sample, there should be between 10 and 170 mg of sorbent per ml of recovery fluid, preferably 10-60 mg per ml of recovery fluid.

Detection System

The detection system comprises an apparatus for detecting and detection media for use with the apparatus. The apparatus and detection media can be based on PCR, RT-PCR, isothermal amplification, gene sequencing or probe hybridization technology. When the detection system uses PCR, the detection system comprises a detection medium which comprises a primer mix comprising at least one primer set complementary to the target nucleic acid, a thermostable polymerase; nucleotide (dNTP); a buffer and one or more detection probes. When the detection system uses RT-PCR, the detection system comprises a detection medium which comprises a primer mix comprising at least one primer complementary to the target RNA; a heat-activated thermostable polymerase; a reverse transcriptase enzyme; nucleotide (dNTP); a buffer; and RNase inhibitor. When the detection system uses isothermal amplification, the detection system comprises a detection medium which comprises a DNA polymerase and a set of four specially designed primers that recognize a total of six distinct sequences on the target nucleic acid. When the detection system uses gene sequencing, the detection system comprises a detection medium which comprises one or more labeling terminators, buffer and appropriate enzymes. When the detection system uses probe hybridization, the detection system comprises a detection medium which comprises an oligonucleotide (synthetic or occurring naturally), that is significantly complementary to a target nucleic acid and is hybridizable thereto. When the detection system uses isothermal amplification, the detection system comprises a detection medium which comprises a DNA polymerase and a set of four specially designed primers that recognize a total of six distinct sequences on the target nucleic acid.

The diagnostic system of the present invention is not limited as to the method of detection and may be used by any method that detects the product of the PCR, RT-PCR, isothermal amplification, gene sequencing or probe hybridization technology. Preferred are PCR and RT-PCR.

In general, PCR thermal cycling includes an initial denaturing step at high temperature, followed by a repetitive series of temperature cycles designed to allow template denaturation, primer annealing, and extension of the annealed primers by the polymerase. Generally, the samples are heated initially for about 2 to 10 minutes at a temperature of about 95° C. to denature the double stranded DNA sample. Then, in the beginning of each cycle, the samples are denatured for about 10 to 60 seconds, depending on the samples and the type of instrument used. After denaturing, the primers are allowed to anneal to the target DNA at a lower temperature, from about 40° C. to about 60° C. for about 20 to 60 seconds. Extension of the primers by the polymerase is often carried out at a temperature ranging from about 60° C. to about 72° C. The amount of time used for extension will depend on the size of the amplicon and the type of enzymes used for amplification and is readily determined by routine experimentation. Additionally, the annealing step can be combined with the extension step, resulting in a two step cycling. Thermal cycling may also include additional temperature shifts in PCR assays. The number of cycles used in any assay may be readily determined by one skilled in the art using routine experimentation. Optionally, a final extension step may be added after the completion of thermal cycling to ensure synthesis of all amplification products.

Following amplification, the amplified nucleotide sequence may be ligated to a suitable vector followed by transformation of a suitable host organism with said vector. One thereby ensures a more readily available supply of the amplified sequence. Alternatively, following amplification, the amplified sequence or a portion thereof may be chemically synthesized for use as a nucleotide probe for use in a hybridization assay, as described below. In either situation, the DNA sequence of the variable region may be established using methods such as the dideoxy method (Sanger, F., et al., *Proc. Natl. Acad. Sci.* 74:5463-5467 (1977)). The sequence obtained is used to guide the choice of the probe for the organism and the most appropriate sequence(s) is/are selected.

In RT-PCR, the reverse transcription is typically carried out in a composition comprising a primer that hybridizes to the target RNA to prime the synthesis of the copy DNA, a mixture of four deoxynucleotide triphosphates (i.e., dATP, dCTP, dTTP, and dGTP), $MgCl_2$, a reverse transcriptase and a reverse transcriptase buffer. Additionally, the composition may optionally contain an RNase inhibitor, such as guanidinium isothiocyanate, diethyl-pyrocarbonate, SuperaseIn™ (Ambion, Inc., Austin, Tex.), RNase Block (Stratagene Corp., La Jolla, Calif.), human placental ribonuclease inhibitor, porcine liver RNase inhibitor (Takara Mirus Bio Company, Madison, Wis.), Anti-RNase (Novagen, Inc., Madison, Wis.), Ribonuclease Inhib III (PanVera Corp., Madison, Wis.), RNAlater™ (Ambion, Inc.), or RNA Protect Bacteria Reagent (Qiagen, Inc., Valencia, Calif.). Suitable reverse transcriptases are well known in the art and include, but are not limited to, HIV Reverse Transcriptase (Ambion, Inc.), Transcriptor Reverse Transcriptase (Roche Applied Science Corp., Indianapolis, Ind.), Thermoscript Reverse Transcriptase (Invitrogen Corp., Carlsbad, Calif.).

Regardless of whether the reverse transcription and amplification are carried out as two steps or one step, the reverse transcription step is run first and typically consists of a single temperature incubation at a temperature of between about 37° C. and about 70° C. Different temperatures are appropriate for different reverse transcriptases and different primers, as is known to one skilled in the art.

A variety of detection methods, which are well known in the art, may be used in the methods disclosed herein. These detection methods include, but are not limited to, standard non-denaturing gel electrophoresis (e.g., acrylamide or agarose), denaturing gradient gel electrophoresis, temperature gradient gel electrophoresis, capillary electrophoresis, and fluorescence detection.

Fluorescence detection methods provide rapid and sensitive detection of amplification products. Fluorescence detection also provides the capability of real-time detection, wherein the formation of amplification products is monitored during the thermal cycling process. Additionally, the amount of the initial target may be quantified using fluorescence detection. Fluorescence detection may be done by adding a nucleic acid-binding fluorescent agent to the reaction mixture either before or after the thermal cycling process. Preferably, the nucleic acid-binding fluorescent agent is an intercalating dye that is capable of non-covalent insertion between stacked base pairs in the nucleic acid double helix. However, non-intercalating nucleic acid-binding fluorescent agents are also suitable.

Non-limiting examples of nucleic acid-binding fluorescent agents useful in the method of this invention are ethidium bromide and SYBR Green I (available from Molecular Probes; Eugene, Oreg.). Addition of the nucleic acid-binding fluorescent agent to the reaction mixture prior to thermal cycling permits monitoring of the formation of amplification products in real-time, as described by Higuchi (U.S. Pat. No. 5,994,056). Thermal cyclers capable of real-time fluorescence measurements are commercially available from companies such as Applied Biosystems (Foster City, Calif.), MJ Research (Waltham, Mass.), and Stratagene (La Jolla, Calif.). Following amplification, confirmation of the amplification product can be assessed by determining the melting temperature of the product using methods know in the art, for example, by generating a melting curve using fluorescence measurement.

Fluorescence detection of amplification products may also be accomplished using other methods known in the art, such as the use of a fluorescently labeled probe. The probe comprises a complimentary sequence to at least a portion of the amplification product. Non-limiting examples of such probes include TaqMan probes (Applied Biosystems) and Molecular Beacons (Goel et al., J. Appl. Microbiol. 99(3):435-442 (2005)). For example, gene sequences for the construction of fluorescently labeled probes for use with TSV primers can be selected by analysis of the TSV genes and test amplicons using commercially available analysis software such as Primer Express® v2.0 (Applied BioSystems Inc., Foster City Calif.), as described in detail in Examples 9 and 10 of WO 2008/024292 A1. Gene sequences for the construction of fluorescently labeled probes for use with WSSV primers disclosed herein can be selected by analysis of the WSSV genes and test amplicons, as described in detail in Examples 11 and 12 of WO 2008/024294 A2. Probe sequences are selected to fall within the proximal ends of the specific test amplicons. The probes may be fluorescently labeled using methods known in the art, such as those described below for labeling hybridization probes. For real time fluorescent detection, probes can be dual labeled. For example, the 5' end of the probe can be labeled with a fluorophore, such as 6FAM™ (Applied BioSystems), and the 3' end can be labeled with a quencher dye, such as 6-carboxytetramethylrhodamine (TAMRA). In the case of a minor groove binding probe, the 3' end can be labeled with a quencher dye and a minor groove binder complex. Fluorescently labeled probes may be obtained from commercial sources such as Applied BioSystems.

In one embodiment, the invention provides a method for quantifying the amount of a target nucleic acid in a sample. In this embodiment, DNA or RNA is provided from a sample suspected of containing the target nucleic acid, and complimentary DNA is generated. The DNA is amplified with at least one pair of the oligonucleotide primers disclosed herein by thermal cycling between at least a denaturing temperature and an extension temperature in the presence of a nucleic acid-binding fluorescent agent or a fluorescently labeled probe. The amount of fluorescence generated by the nucleic acid-binding fluorescent agent or the fluorescently labeled probe is measured during thermal cycling. From the fluorescence measurements, a threshold cycle number is determined at which the amount of fluorescence generated by the nucleic acid-binding fluorescent agent or the fluorescently labeled probe reaches a fixed threshold value above a baseline value. The cycle threshold number is referred to herein as the CT number or value. The CT number can be determined manually or determined automatically by the instrument. To determine the CT number, the baseline fluorescence is determined for each sample during the initial amplification cycles. A mathematical algorithm is then employed to establish what a statistically significant change in fluorescence would need to be for the fluorescence signal to be above the background. The cycle number at which the florescence exceeds this threshold is referred to as the CT number. Typically, the more DNA present in the sample at the start of the thermal cycling, the fewer number of cycles it will take to reach the threshold value.

Therefore, the CT number is inversely related to the initial amount of the target nucleic acid in the sample. After the CT number for the sample is determined, the amount of target nucleic acid originally present in the sample can be calculated by comparing the cycle threshold number determined for the target nucleic acid in the sample with a standard curve of the cycle threshold number versus the logarithm of template concentration determined using standard solutions of known concentration, as is well known in the art.

The following describes target nucleic acid sequences for WSSV and TSV. It will be appreciated by those skilled in the art that other target nucleic acid sequences can be detected or identified using the method, kit and diagnostic system of this invention.

Sequence Descriptions

The various embodiments of the invention can be more fully understood from the following detailed description and the accompanying sequence descriptions, which form a part of this application.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5 (a-bis), and Section 208 and Annex C of the Administrative Instructions). The symbols and format used for nucleotide and amino acid sequence data comply with the rules set forth in 37 C.F.R. §1.822.

SEQ ID NOs: 1-8 are the nucleotide sequences of WSSV diagnostic primers useful for detection of WSSV.

SEQ ID NOs: 9-12 are the nucleotide sequences of synthetic WSSV templates described in the General Methods section of the Examples. These sequences are also the nucleotide sequences of amplification products obtained using pairs of WSSV diagnostic primers disclosed herein.

SEQ ID NOs: 13-18 are the nucleotide sequences of Taura Syndrome Virus (TSV) diagnostic primers useful for detection of TSV.

SEQ ID NOs 19-21 are the nucleotide sequences of synthetic TSV templates described in the General Methods section of the Examples. These sequences are also the nucleotide sequences of amplification products obtained using pairs of TSV diagnostic primers disclosed herein.

The sequences, amplification products, and diagnostic primers are described, with respect to WSSV, IHHNV, TSV and *Vibrio harveyi* are described more fully in WO 2008/024294 (for WSSV); WO 2008/024293 (for IHHNV); WO 2008/024292 (for TSV); and WO 2008/048673 (for *Vibrio harveyi*).

Generally the two primers are mixed with the sample DNA, a mixture of four deoxynucleotide triphosphate (i.e., dATP, dCTP, dTTP, and dGTP), a thermostable DNA polymerase, such as Taq DNA polymerase, in a buffer solution. This mixture is then thermal cycled using a thermal cycler instrument to amplify the desired target region. Thermal cyclers are commercially available from many sources (e.g., Applied Biosystems, Inc., Foster City, Calif.; Brinkmann Instruments, Inc., Westbury, N.Y.; MJ Research, Inc., Waltham, Mass.; Stratagene Corp., La Jolla, Calif.).

Viral Genomes

The white spot syndrome virus (WSSV), also known as the white spot baciliform virus (WSBV), is a major shrimp pathogen with a high mortality rate and a wide host range. The complete genome of WSSV has been sequenced (van Hulten, et al., Virology 286:7-22 (2001); and Yang, et al., J. Virol. 75:11811-11820 (2001)). The genome consists of double stranded, circular DNA containing 305,107 base pairs (bp) and 181 open reading frames (ORFs) (GenBank AF332093). There are at least 12 variants of WSSV found in Thailand that are distinguished by differences in multiple repeat lengths in ORF 94 (Wongteerasupaya, et al., Dis. Aquat. Org. 54:253-257 (2003)).

The taura syndrome virus (TSV) is a major shrimp pathogen with a high mortality rate and a wide host range. The complete genome of TSV has been sequenced (GenBank AF277675). The genome consists of single stranded RNA containing 10,205 bases and 2 open reading frames (ORFs).

WSSV Diagnostic Primer Sequences

Disclosed herein are diagnostic primer sequences useful in a variety of assay formats for high sensitive detection of WSSV. These primers are directed to regions of the WSSV genome which are diagnostic for WSSV detection.

Primer sequences were empirically identified using a series of "in silica" (i.e., computer based) sequence analysis tools. In this process, a database was assembled containing all known WSSV sequences. These sequences were first aligned and then analyzed for primer sites using Vector NTI® software (InforMax, Inc., Bethesda, Md.) based on homology with other WSSV sequences, a specified amplicon length, salt concentration, Tm (melting temperature), C+G content and freedom from hairpin and secondary structure parameters. Prospective primers were then screened against GenBank sequences. Those primers established to contain less than 5 bases of homology with other non-target gene sequences were selected for experimental investigation of PCR amplification efficiency and minimal primer-dimer formation. Primers showing both high amplification efficiency and minimal primer-dimer formation were selected for testing with a panel of DNA isolated from shrimp infected with various shrimp pathogens and DNA from shrimp certified to be disease-free. Those primers amplifying all WSSV strains and showing no response to both DNA from shrimp infected with non-WSSV pathogens and to DNA isolated from different species of certified disease-free shrimp were selected as useful primers.

The primer sequences useful in the detection of WSSV and their location in the WSSV genome are given in Table 1. These primers were synthesized using standard phosphoramidite chemistry or may be purchased from companies such as Sigma Genosys, LP.

TABLE 1

WSSV Diagnostic Primer Sequences

| Primer, Direction | SEQ ID NO: | ORF | WSSV Genome Location (GenBank AF332093) |
|---|---|---|---|
| WSSV77F, Forward | 1 | 77 | 61335-61358 |
| WSSV77R, Reverse | 2 | 77 | 61420-61443 |
| WSSV54F, Forward | 3 | 54 | 31287-31309 |
| WSSV54R, Reverse | 4 | 54 | 31391-31414 |
| WSSV56F, Forward | 5 | 56 | 33145-33168 |

TABLE 1-continued

WSSV Diagnostic Primer Sequences

| Primer, Direction | SEQ ID NO: | ORF | WSSV Genome Location (GenBank AF332093) |
|---|---|---|---|
| WSSV56R, Reverse | 6 | 56 | 33269-33292 |
| WSSV130F, Forward | 7 | 130 | 146110-146132 |
| WSSV130R, Reverse | 8 | 130 | 146212-146234 |

The amplicon sequence for each of the WSSV primer set listed in Table 1 are shown in Table 2. For use as positive controls, the WSSV templates were synthesized using standard methods. The concentration and copy number of the synthetic template preparations were determined from spectrophotometric measurements at 260 nm ($OD_{260}$). The templates were diluted to specific copy numbers in purified water and were used as the positive controls and standards for assay quantification. Table 2 displays the genome locations, sequence identification, and lengths of template targets. The sequences of the primers useful for WSSV detection are given as SEQ ID NOs: 1-8.

TABLE 2

Template Sequences

| Template | Size (bp) | SEQ ID NO: | WSSV Genome Location (GenBank AF332093) |
|---|---|---|---|
| WSSV 77T | 109 | 9 | 61335-61443 |
| WSSV 54T | 128 | 10 | 31287-31414 |
| WSSV 56T | 148 | 11 | 33145-33292 |
| WSSV 130T | 125 | 12 | 146110-146234 |

TSV Diagnostic Primer Sequences

Listed in Table 3 are diagnostic primer sequences useful in a variety of assay formats for high sensitive detection of TSV. These primers are directed to regions of the TSV genome which are diagnostic for TSV detection.

Primer sequences for TSV were empirically identified using a series of "in silica" (i.e., computer-based) sequence analysis tools. In this process, a database was assembled containing all known TSV sequences. These sequences were first aligned and then analyzed for primer sites using Vector NTI® software (InforMax Inc., Bethesda, Md.) based on homology with other TSV sequences, a specified amplicon length, salt concentration, Tm (melting temperature), C+G content and freedom from hairpin and secondary structure parameters. Prospective primers were then screened against GenBank sequences. Those primers established to contain less than 5 bases of homology with other non-target gene sequences were selected for experimental investigation of PCR amplification efficiency and minimal primer-dimer formation. Primers showing both high amplification efficiency and minimal primer-dimer formation were selected for testing with a panel of DNA isolated from shrimp infected with various shrimp pathogens and DNA from shrimp certified to be disease free. Those primers amplifying all TSV strains and showing no response to both DNA from shrimp infected with non-TSV pathogens and to DNA isolated from different species of certified disease free shrimp were selected as useful primers.

The primer sequences found to be useful in the detection of TSV and their location in the TSV genome are given in Table 3. These primers may be synthesized using standard phosphoramidite chemistry or may be purchased from companies such as Sigma Genosys, LP.

TABLE 3

TSV Diagnostic Primer Sequences

| Primer, Direction | SEQ ID NO: | ORF | TSV Genome Location (GenBank AF277675) |
|---|---|---|---|
| TSV2F, Forward | 13 | 1 | 475-498 |
| TSV2R, Reverse | 14 | 1 | 568-592 |
| TSV3F, Forward | 15 | 1 | 4953-4976 |
| TSV3R, Reverse | 16 | 1 | 5053-5075 |
| TSV5F, Forward | 17 | 2 | 7377-7401 |
| TSV5R, Reverse | 18 | 2 | 7470-7494 |

The amplicon sequence for each of the TSV primer set listed in Table 3 are shown in Table 4. For use as positive controls, the TSV templates were synthesized using standard methods. The concentration and copy number of the synthetic template preparations were determined from spectrophotometric measurements at 260 nm ($OD_{260}$). The templates were diluted to specific copy numbers in purified water and were used as the positive controls and standards for assay quantification. Table 4 displays the genome locations, sequence identification, and lengths of template targets. The sequences of the primers useful for TSV detection are given as SEQ ID NOs: 13-18.

TABLE 4

Template Sequences

| Template | Size (bp) | SEQ ID NO: | TSV Genome Location (GenBank AF277675) |
|---|---|---|---|
| TSV 2T | 118 | 19 | 475-592 |
| TSV 3T | 123 | 20 | 4953-5075 |
| TSV 5T | 118 | 21 | 7377-7494 |

EXAMPLES

The following Examples aid in illustrating the overall utility of the sample processing method for detection of an DNA target nucleic acid and a RNA target nucleic acid. It should be understood that these Examples, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations is as follows: "sec" means second(s), "min" means minute(s), "hr" means hour(s), "d" means day(s), "µL" means microliter(s), "mL" means milliliter(s), "L" means liter(s), "µM" means micromolar, "mM" means millimolar, "nM" means nanomolar, "M" means molar, "mmol" means millimole(s), "µmol" mean micromole(s), "ng" means nanogram(s), "fg" means femtogram(s), "µg" means microgram(s), "mg" means milligram(s), "g" means gram(s), "nm" means nanometer(s), "mU" means milliunit(s), "in." means inches, "U" means unit(s), "rxn" means reaction(s), "OD" means optical density, "$OD_{260}$" means the optical density measured at a wavelength of 260 nm, "$OD_{280}$" means the optical density measured at a wavelength of 280 nm, "$OD_{280/260}$" means the ratio of the $OD_{280}$ value to the $OD_{260}$ value, "rpm" means revolutions per minute, "CT" means the cycle number at which the buildup in fluorescence in the reaction exceeds the detection threshold, and "SPF" means certified specific pathogen free.

General Methods

Standard recombinant DNA and molecular cloning techniques used in the Examples are well known in the art and are described by Sambrook, J., Fritsch, E. F. and Maniatis, T., *Molecular Cloning: A Laboratory Manual*, Cold Spring Harbor Laboratory Press, Cold Spring Harbor, N.Y., 1989; by T. J. Silhavy, M. L. Bennan, and L. W. Enquist, *Experiments with Gene Fusions*, Cold Spring Harbor Laboratory Press, Cold Spring Harbor, N.Y., 1984; and by Ausubel, F. M. et al., *Current Protocols in Molecular Biology*, Greene Publishing Assoc. and Wiley-Interscience, N.Y., 1987.

Analysis of genome sequences and primer designates was accomplished using the Vector NTI® Software Suite available from InforMax, Inc. (Bethesda, Md.).

Enzymes and reagents used herein were purchased from the following vendors:
Applied Biosystems, Inc.: AmpliTaq (Catalog No. N808-0160);
New England Biolabs, Inc., Beverly, Mass.: deoxynucleotide solution mix (Catalog No. N0447S);
Sigma Genosys, LP: Oligonucleotides;
Invitrogen Corp., Carlsbad, Calif.: 4% Agarose E-gels (Catalog No. G6018-02);
Qiagen, Inc.: Proteinase K (Catalog No. 19131); and RNase A, DNase-free (Catalog No. 19101).

Kit elements and reagents were purchased from the following vendors: SYBR® Green PCR Master Mix (Applied Biosystems, Inc.; Catalog No. 4309155); and QIAamp DNA Mini Kit (Qiagen, Inc.; Catalog No. 51304).

Shrimp Samples

All shrimp DNA samples were obtained from Donald V. Lightner, Department of Veterinary Science and Microbiology, University of Arizona, Tucson, Ariz. 85721, USA. These included samples from certified disease free shrimp (SPF) and infected shrimp containing *Penaeus monodon*-type baculoviruses (MBV), Taura syndrome virus (TSV), white spot syndrome virus (WSSV), yellow head virus of *P. monodon* (YHV), Infectious Hypodermal and Hematopoietic Necrosis virus (IHHNV) and Infectious Myonecrosis virus (IMNV).

Templates and Primers

For sake of demonstrating recovery and detection of a DNA virus target nucleic acid from shrimp tissues, primers were developed and synthesized to regions of DNA oligonucleotide genome of the White Spot Syndrome Virus (WSSV) DNA genome (GenBank Accession Number AF332093; Yang, F., et al., *J. Virology* 75 (23), 11811-11820 (2001)) and were synthesized using standard phosphoramidite chemistry or purchased commercially (Sigma Genosys, LP).

For sake of demonstration recovery and detection of an RNA virus target nucleic acid from shrimp, primers were developed and synthesized to the oligonucleotide sequences of Taura Syndrome Virus (TSV) genome (GenBank Accession Number AF277675); Mari, J., Poulos, B. T., Lightner, D. V. and Bonami, J. R., *J. Gen. Virol.* 83 (Pt 4):915-926 (2002). These were synthesized from bases 475 to 592 and 4953 to 5076 and 7377 to 7495, respectively. The synthetic TSV targets were synthesized using standard phosphoramidite chemistry or purchased commercially (Sigma Genosys, LP). The synthetic TSV targets were used in a single reaction as the positive control and standards for quantification in real-time RT-PCR assay.

Example 1

This Example shows the application of the method of this invention and vessel for processing shrimp samples and detection of WSSV target nucleic acid in the different shrimp tissues. Since WSSV infects tissues/organs of mesodermal and ectodermal origin, a variety of shrimp tissues of *P. monodon* were obtained from Dr. Lightner. Tissues were collected both from shrimp infected with WSSV and SPF shrimp certified to be WSSV-free. The samples included (a) hemolymph, (b) pleopods, (c) gills, and (d) tail muscle. Extraction control portions of the same samples were processed with a reference sample extraction method (QIAamp DNA Mini Kit (Qiagen, Inc.; Catalog No. 51304).

The amount of shrimp tissue processes per sample varied between samples. For shrimp tissue, the weight of sample processed ranged from 50 to 200 mg/sample. For hemolymph 5 to 50 µL/sample were processed.

Samples were processed by adding each solid tissue and hemolymph to a 3 in.×3 in. (76×76 mm) 4 mil (0.10 mm) polypropylene zipper lock bag (Associated Bag, Inc., Milwaukee, Wis.) for use as the flexible vessel. For hemolymph, the hemolymph was added directly to the bag.

No crushing was performed for hemolymph samples. For samples of pleopods, gills, and tail muscle, the tissue was crushed in the bag by applying force to the bag surface or hitting the bag using the flat end of a plastic container (1 in.×1 in., 25 mm×25 mm, diameter). The crushing action was repeated about 5 times over a period about 10 sec.

Five milliliters of extraction fluid (50 mM Tris-HCl, 3.0 mM $MgCl_2$, 28 mM KCl, 0.1% Triton X-100 surfactant) at room temperature was then added to each sample and the zip lock on the bag was closed.

Tissue samples were then mixed and suspended in the extraction fluid to provide recovery liquid by shaking or by repeatedly squeezing the bag. The bags were allowed stand for about five minutes. During this time, particulates were observed to settle out.

For detection, the bags were opened and 50 µL of the recovery fluid was transferred to a lyophilized PCR reagent formulation (25 mM dNTP, 0.005 µL SYBR Green I(R), 0.24 µg BSA, 1.8 Units Amplitaq™, excipient and 18 pmole/rxn of forward and reverse WSSV primers (3 and 4). PCR was performed using the following thermal cycling program: denaturation 95° C. (5 min), 35 cycles 95° C. (30 s), 58° C. (30 s), 72° C. (60 s), 1 cycle 72° C. (60 s), 4° C. (infinity). Test result were then analyzed using by electrophoresis using Invitrogen Corp., Carlsbad, Calif.: 4% Agarose E-gels (Catalog No. G6018-02).

A comparison of detection results from the tissues processed by this method and the same tissue processed by the reference sample extraction method ((QIAamp DNA Mini Kit (Qiagen, Inc.; Catalog No. 51304) showed comparable results. WSSV was detected in each sample that contained the virus. With gill tissue some PCR inhibition was detected. Thus, the method of this invention can be used advantageously with less time and conveniently over conventional methods for the white spot syndrome virus (WSSV).

Example 2

This Example shows that the method and vessel of this invention can be effectively used in the processing and recovery of target RNA for detection.

A similar experiment to Example 1 is set up with SPF control shrimp and shrimp infected with TSV virus. Since TSV infects tissues/organs of mesodermal and ectodermal origin, a variety of shrimp tissues of *P. monodon*, are used. TSV samples are obtained from Dr. Lightner. Tissues are collected both from shrimp infected with TSV and SPF shrimp certified to be WSSV-free.

The samples included (a) hemolymph, (b) pleopods, (c) gills, and (d) tail muscle. Extraction control portions of the same samples were processed with a reference sample extraction method (QIAamp DNA Mini Kit (Qiagen, Inc.; Catalog No. 51304).

The amount of shrimp tissue processes per sample can vary between samples. The weight of sample for shrimp tissue ranges from 50 to 200 mg/sample. For hemolymph samples, 5 to 50 µL/sample is processed.

Samples are processed by adding each solid tissue and hemolymph to a 3 in.×3 in. (76 mm×76 mm), 4 mil (0.10 mm) polypropylene zipper lock bag (Associated Bag Inc., Milwaukee, Wis.). For hemolymph, the hemolymph is added directly to the bag. No crushing is performed. For pleopods, gills, and tail muscle, the tissue is crushed in the bag by applying force to the bag surface or hitting the bag using the flat end of a plastic container (1 in., 25 mm in diameter). The crushing action is repeated about 5 times over a period of about 10 sec. Five milliliters of extraction fluid (50 mM Tris-HCl, 3.0 mM $MgCl_2$, 28 mM KCl, 0.1% Triton X-100) at room temperature can then be added to sample and the zip lock closed. Tissue samples can be mixed and suspended in the recovery liquid by shaking or by repeatedly squeezing the bag. The bags are allowed to stand for about five minutes. During this time particulates tend to settle out.

For detection, the bags are opened and 50 µL of the recovery fluid is transferred to a lyophilized RT-PCR reagent formulation. The formulation is prepared by adding to 25 µL of the SYBR® Green PCR Master Mix (Applied Biosystems, Inc.; Catalog No. 4309155), 31.3 nM each of the appropriate TSV forward primer 13 and 62.5 nM of the reverse primer 14, 12.5 U of Multiscribe Reverse transcriptase, 20 U of Multiscribe RNase inhibitor.

RT-PCR is performed using the following thermal cycling program: an initial step of 48° C. for 30 min followed by an initial denaturing step of 95° C. for 10 min and then 35 cycles using a temperature program of 95° C. for 15 sec and 60° C. for 1 min. Denaturation 95° C. (5 min), 35 cycles 95° C. (30 s), 58° C. (30 s), 72° C. (60 s), 1 cycle 72° C. (60 s), 4° C. (infinity), then thermal cycle with an initial step of 48° C. for 30 min followed by an initial denaturing step of 95° C. for 10 min and then 40 cycles using a temperature program of 95° C. for 15 sec and 60° C. for 1 min. and a final cycle 72° C. (60 s), 4° C. (infinity).

Test result can be analyzed using by electrophoresis using Invitrogen Corp., Carlsbad, Calif.: 4% Agarose E-gels (Catalog No. G6018-02).

An comparison of the sample results that show TSV could indicate that tissues processed by the method of this invention and the same tissue processed by the reference sample extraction method RNeasy fibrous tissue Mini Kit (Qiagen, Inc. Catalog No. 74704) show comparable results in each sample which contain the TSV virus. With gill tissue some PCR inhibition is detected. Thus, the method of this invention can be used advantageously with less time and conveniently over conventional methods for the taura syndrome virus (TSV).

What is claimed is:

1. A method for collecting, processing, and analyzing a target nucleic acid from a sample comprising:
   (a) providing a sample wherein the sample is a shrimp tissue comprising nucleic acids, wherein the target nucleic acid is diagnostic of a shrimp pathogen-comprising white spot syndrome virus;
   (b) transferring the sample to a flexible-walled vessel, which can be inverted so that the exterior wall becomes the interior wall and in which sample materials can be agitated and suspended by applying and releasing external pressure to the walls;
   (c) adding an extraction fluid to the vessel;
   (d) processing the sample with the extraction fluid and one or more treatment reagents in the vessel to release nucleic acid from the sample to solubilize the nucleic acid and produce a recovery fluid;
   (e) filtering the recovery fluid produced in step (d) wherein the vessel contains filter media to remove particulates; and
   (f) transferring a portion of the recovery fluid or product from step (e) to a suitable detection system for detection of the target nucleic acid, wherein the detection system for detection of the target nucleic acid uses PCR or RT-PCR for amplification of the target nucleic acid using diagnostic primer sequences for the shrimp pathogen, and wherein the diagnostic primer sequences for the white spot syndrome virus are selected from: (i) SEQ ID NO: 1 and SEQ ID NO: 2; (ii) SEQ ID NO: 3 and SEQ ID NO: 4; (iii) SEQ ID NO: 5 and SEQ ID NO: 6; and (iv) SEQ ID NO: 7 and SEQ ID NO: 8.

2. The method of claim 1 wherein the sample comprises a solid material and prior to step (c) the process comprises a step of crushing the sample in the flexible-walled vessel and the processing step (d) comprises mixing and macerating the sample with the extraction fluid and treatment reagent(s) in the vessel to aid in release of the nucleic acid.

3. The method of claim 1 wherein the one or more treatment reagents comprises a lysing agent, which comprises a detergent, an enzyme, or a combination thereof.

4. The method of claim 3 wherein the one or more treatment reagents further comprises a buffer having pH in the range of 7 to 7.8, magnesium chloride, and potassium chloride.

* * * * *